(12) United States Patent
Virtanen (10) Patent No.: US 6,196,979 B1
(45) Date of Patent: Mar. 6, 2001

(54) CASSETTE AND APPLICATOR FOR BIOLOGICAL AND CHEMICAL SAMPLE COLLECTION

(75) Inventor: Jorma A. Virtanen, Irvine, CA (US)

(73) Assignee: Burstein Technologies, Inc., Irvine, CA (US)

( * ) Notice: Subject to any disclaimer, the term of this patent is extended or adjusted under 35 U.S.C. 154(b) by 0 days.

(21) Appl. No.: 09/139,213

(22) Filed: Aug. 24, 1998

(51) Int. Cl.[7] ........................................................ A61B 5/00
(52) U.S. Cl. ............................................................ 600/573
(58) Field of Search ........................... 600/562, 564–567, 600/573, 576, 583, 584; 422/58, 68.1

(56) References Cited

U.S. PATENT DOCUMENTS

| | | | |
|---|---|---|---|
| 4,142,517 | * 3/1979 | Stavropoulos et al. | 600/567 |
| 4,959,196 | 9/1990 | Moisson | 422/82.05 |
| 5,133,930 | 7/1992 | Biro et al. | 606/182 |
| 5,518,006 | 5/1996 | Mawhirt et al. | 128/770 |
| 5,638,828 | * 6/1997 | Lauks et al. | 600/573 |
| 5,800,781 | * 9/1998 | Gavin et al. | 600/573 |
| 5,892,577 | 4/1999 | Gordon | 356/73 |
| 5,922,617 | 7/1999 | Wang et al. | 436/518 |
| 5,971,941 | * 10/1999 | Simons et al. | 600/573 |
| 6,030,581 | 2/2000 | Virtanen | 422/68.1 |

FOREIGN PATENT DOCUMENTS

| | | | |
|---|---|---|---|
| 0 417 305 A1 | 3/1991 | (EP) | G01N/35/00 |
| WO 97/21090 | 6/1997 | (WO) | G01N/21/07 |

\* cited by examiner

*Primary Examiner*—Max Hindenburg
(74) *Attorney, Agent, or Firm*—Oppenheimer Wolff & Donnelly LLP (57) ABSTRACT

A biological sample collection unit for a centrifugal analyzer disk is disclosed. This unit consists of a flat cassette and an applicator that holds and controls the cassette during sample collection and during placement of the cassette into the analyzer disk.

16 Claims, 8 Drawing Sheets

CASSETTE AND APPLICATOR FOR BIOLOGICAL AND CHEMICAL SAMPLE COLLECTION

FIELD OF THE INVENTION

The present invention relates to a liquid biological sample collection unit that is suitable for using with a centrifugal analyzer disk. More particularly, the sample collection unit consists of a relatively flat cassette and optionally an applicator that holds and controls the cassette during sample collection and is used to place the casette into the analyzer.

BACKGROUND

Biological samples are primarily taken into evacuated glass or plastic tubes, such as Vacutainer™ tubes (Becton Dickinson) from a subject. Normally, a double ended needle is first inserted into a subject's vein, and the other end of the needle is used to puncture a septum in an adjoining evacuated tube. Alternatively, two needles may be connected by a tube. In such an arrangement, a first needle may be inserted into a vein, while a second needle goes through a septum of a sample collection tube. The blood sample so obtained must be transferred to various analyzers from this tube. This represents additional work, may lead to contamination or mixup of the samples, and may present health hazards for laboratory staff. It is preferable to take biological samples from a subject directly into vessels that may be incorporated directly into analyzers.

There is a trend in the art to use analyzers that can perform multiple assays from a very small biological sample. An analyzer disk such as a Bio-Compact Disk™ (Burstein Laboratories, Inc.) provides the capacity for hundreds or even thousands of DNA tests, immunoassays and other clinical tests to be conducted simultaneously using a small sample volume. Such devices make it feasible to simultaneously perform multiple analyses of biological samples from a single small sample. Thus, it is important to improve the collection of biological samples and the transfer of the same into suitable containers for rapid and efficient sample analysis.

Some have recognized such a need especially in view of the significant health hazards involved with obtaining biological samples. Automatic skin pricking lancet devices have been developed to replace traditional needles. Usually these lancet devices have an extractable spring loaded blade or dart for pricking the patient's skin upon pressing a button, lever mechanism or switch. The blade then automatically retracts back into the device housing thereby preventing the individual obtaining the biological sample from the subject from being pricked by the blade. A sample of blood is normally then extracted from the subject using a pipette to extract the blood sample by capillary action. Alternatively, the subject may drop a sample into a collection container after being pricked. Examples of such pricking devices may be found in Biro et al., U.S. Pat. No. 5,133,730.

Moisson, U.S. Pat. No. 4,959,196 discloses an autopricking device integral with an assembly for testing blood samples to evaluate the presence and concentrations of particular substances. After the patient's finger is pricked with this device, the patient deposits a drop of blood onto a strip with a reactive agent. The blood is then automatically tested by means of a reflectometer integral with the assembly. This device lacks a means to transfer blood to a more sophisticated analyzer for additional testing.

Mawhirt et al., U.S. Pat. No. 5,518,006 disclose a blood sampling apparatus for collecting and storing a blood sample from a patient for subsequent transfer to an external blood receiving means. Such a blood sampling apparatus for collecting and transferring blood is not specifically adapted for using with a disk suitable for engagement with a centrifugal analyzer such as a CD or DVD player. Moreover, it is not adapted to be used in conjunction with an applicator for easy blood collection.

SUMMARY OF THE INVENTION

In one aspect the present invention provides an apparatus for collecting biological samples so that the samples can be transferred directly from a patient into an analyzer without intermediate processing. The apparatus is suitable for use with centrifugal player disks such as CD and DVD disks and is specifically designed to facilitate transfer of a biological sample from a subject into a CD or DVD disk for analysis by an analyzer adapted to obtain information from the same. In some embodiments, the apparatus is a cassette that is flat so that it fits into a compact-disk shaped analyzer disk. In some embodiments, the apparatus is evacuated. The apparatus may optionally contain one or more reagents and active components such as batteries, pumps, light sources, assay elements and microprocessors that may be used to deliver a sample into an analyzer or to assist in performing assays.

In another aspect, the invention provides an applicator for handling the cassette in order to facilitate taking a sample and inserting the cassette into an analyzer. The applicator is adapted to accommodate the cassette and to disengage the cassette after the biological sample is obtained. Preferably, the applicator is substantially pen-shaped and is preferably partially transparent so that the cassette may be viewed from outside the applicator. Also, preferably the applicator contains one or more compression rods that may be operably linked to a means for controlling the same such as a button. The compression rods may be used to evacuate or create a vacuum within the cassette, and they may be used to guide the cassette out of the applicator.

BRIEF DESCRIPTION OF THE DRAWINGS

FIG. 2 provides a more detailed top and side view of a representative evacuated sample cassette according to the present invention. The cassette is formed from a lid 3 having a bottom 2 and walls defining a cavity 4. Regardless of the shape or size, a means for obtaining a biological sample such as a needle 1 is provided. In addition, the needle may be in relation with a stopper 5 in such a manner as to limit penetration into the subject. The needle 1 may be in relation to the cavity 4 of the cassette through a septum 7. The walls of the cassette may provide a means for lodging the cassette into position with the applicator or with an analyzer such as corrugated edges 10. Optionally, the cassette may comprise or be integrally associated with a plug 8. Such a plug may be useful for transferring biological samples into an analyzer.

FIG. 3 represents an exemplary conduit means that allows a biological sample to travel from a subject into a sample cassette. There is provided a means for obtaining a biological sample such as a needle 1. Instead of a needle, any of the pricking means provided by the prior art might be provided in conjunction with means for passing the biological sample from the subject into the cavity 4 of the cassette.

FIG. 4 represents front and side views of a representative applicator used in conjunction with a sample cassette.

FIG. 5 represents an exemplary mechanical rectifier designed to provide for movement of a sample cassette in only one direction relative to an applicator.

FIG. 7A depicts an empty analyzer. FIG. 7B depicts a cassette filled with a biological sample. FIG. 7C depicts engagement of the filled cassette with the analyzer. FIG. 7D depicts evacuation of the biological sample into the analyzer after the cassette and analyzer are engaged. The cassette may have a wall or partition 22 in its cavity 4 that may function to circulate incoming reagent solutions through a first tube 26, a needle 24 and a septum 20 so that the biological sample is flushed out of the sample cassette through a second tube 27. Air may enter into the sample cassette through a third tube 25, a needle 23 and a septum 21.

FIG. 8 depicts an exemplary applicator having a sample cassette in accordance with the present invention.

FIG. 9 depicts an exemplary cassette in a substantially syringe shape.

DETAILED DESCRIPTION OF THE INVENTION

In one aspect the present invention provides an apparatus for collecting biological samples so that the biological samples can be transferred directly from a subject into an analyzer without intermediate processing. The apparatus is preferably flat, the maximum thickness being dictated by the properties of commercially available DVD- or CD-players or the like. Currently the thickness of a CD must be less than about 2.4 mm. Thus, in preferred embodiments, the apparatus forms a cassette for engaging with a CD or DVD player. The shape and size of the cassette may be highly variable. Triangular or oval shapes are representative of many embodiments although some asymmetry is often preferred in order to prevent misplacement of the cassette. When an applicator is used in conjunction with a sample cassette, asymmetry does not provide particular advantage because the applicator can be marked to show the proper orientation. The sample cassette may be designed so that it can be put onto an analyzer disk such as a CD or DVD disk either side up. The cassette cavity accommodates a relatively small sample volume, usually from about $0.1 \mu l$ to about $800 \mu l$, so that the inner dimensions of the cassette usually vary between about 0.1 mm×1 mm×1 mm to about 2.0 mm×10 mm×40 mm. Because of the geometric variability of the sample cassette and because the shape is often not rectangular, these dimensions are provided as rough examples and are not to be construed as limiting.

Figure 1:
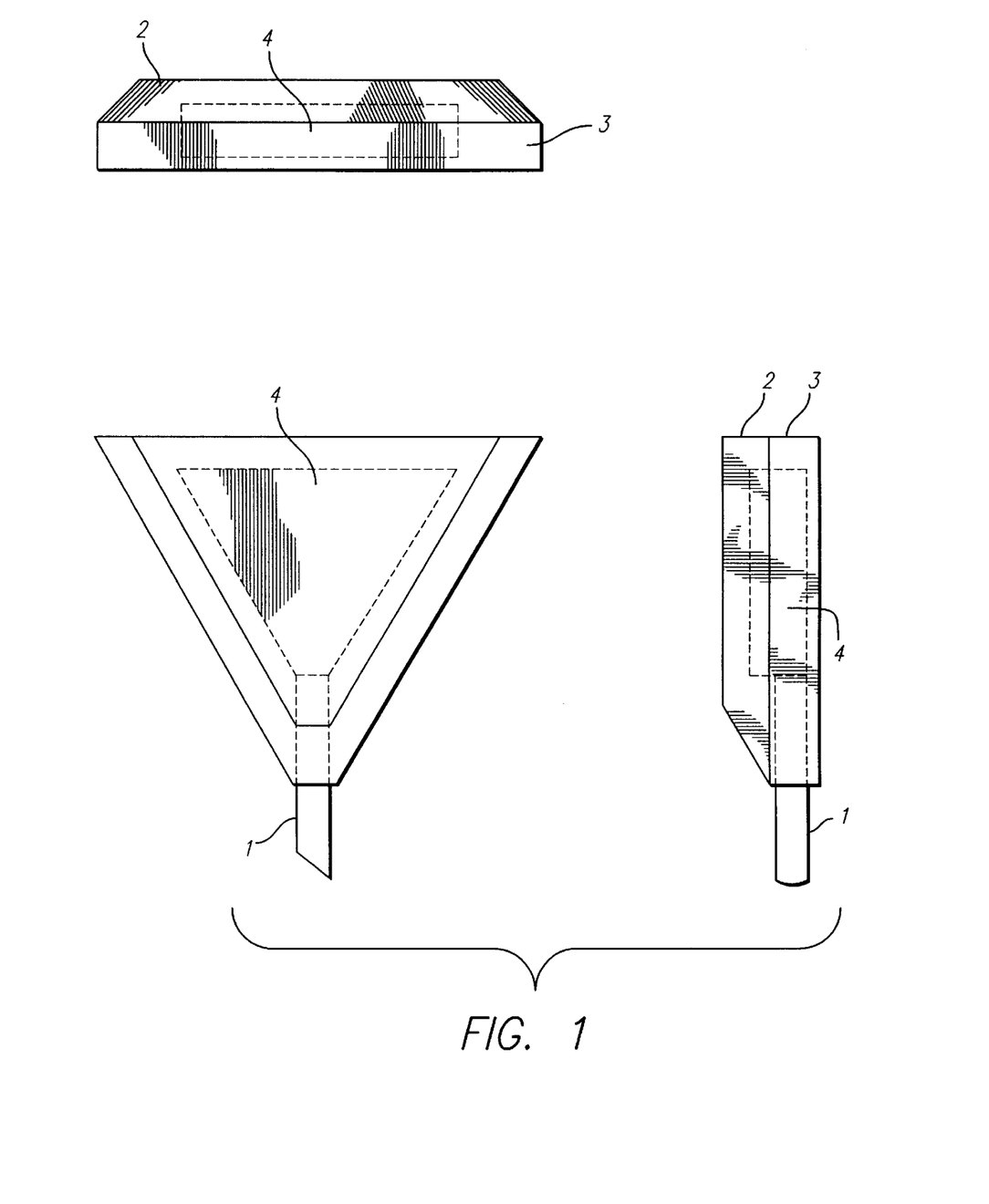
FIG. 1 provides a top and a side view of a representative triangularly shaped cassette according to the present invention. The cassette is formed from a lid 3 having a bottom 2 and walls defining a cavity 4. Regardless of the shape or size, a means for obtaining a biological sample such as a needle 1 is provided.

A triangular sample cassette according to the present invention is depicted in FIG. 1. This sample cassette comprises a lid 3 having a bottom 2 and walls defining a cavity 4. Regardless of the shape or size, a means for obtaining a biological sample such as a needle 1 is provided. Such a sample cassette may be made of glass, a ceramic, plastic, rubber, metal, or a combination of these or other suitable materials alone or in combination. Plastics such as polyethylene, polypropylene, polyvinylchloride, polymethylmethacrylate, polycarbonate, silicone and cellulose acetate are currently preferred. A plastic can be coated from inside, outside or between layers by a metal, such as gold, silver or aluminum. A needle 1 is preferably made of a stainless steel or comparable material. Parts of the sample cassette that may be in contact with a biological sample or reagents can be further coated by one or more detergents, proteins, carbohydrates, oligo- and polynucleotides, or synthetic polymers to make the surface substantially nonadsorbing. Such a coating can be attached covalently or by using van der Waals forces or hydrogen or ion bonding. Nonionic detergents, such as Tween-20, are especially preferred detergents. Proteins that may be used in coating portions of the sample cassette include albumin, collagen, fibrin, avidin, immunoglobulins, streptavidin, or fragments or analogs of any of these or other suitable proteins. Carbohydrates that may be used in coating portions of the sample cassette include cellulose, starch, dextran and heparin. Synthetic polymers that can be used for coating portions of the sample cassette include polyvinylalcohol, polylactic acid and polyethylene glycol. In preferred embodiments, surface bound oligonucleotides and polynucleotides may be used to attach a second layer of molecules and particles that are conjugated with complementary oligonucleotides.

Figure 2:
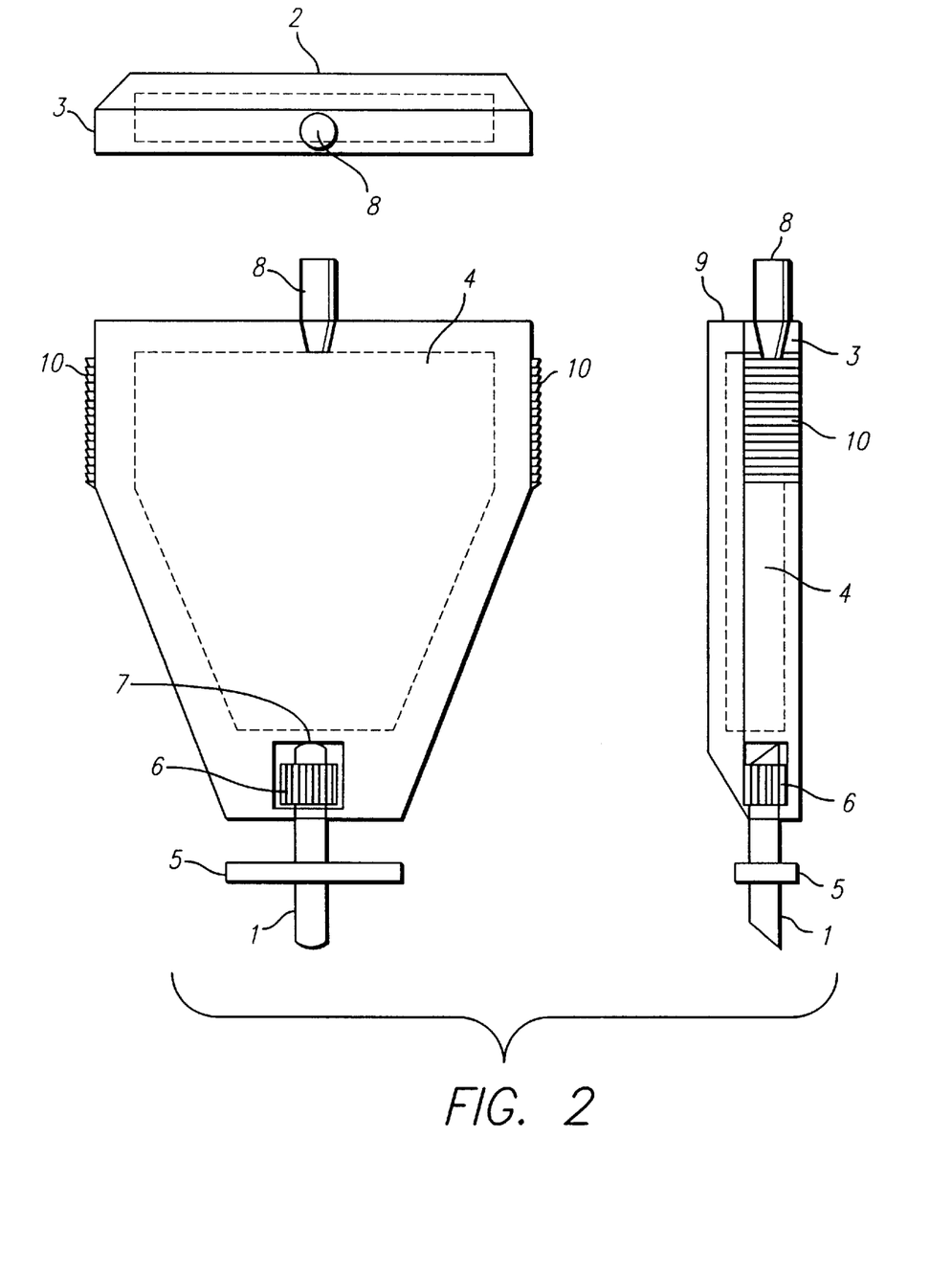
Figure 3A:
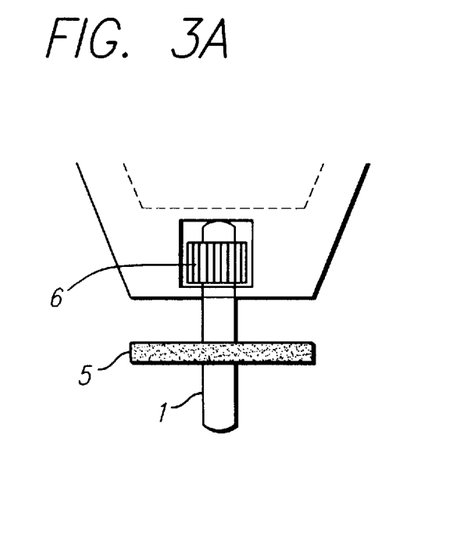
FIG. 3A depicts a needle 1 having an optional stopper 5 spaced around or in relation to the needle 1 so as to prevent penetration of the needle to an undesirable depth inside the subject. Also present is a septum 7 designed to integrate the needle 1 with the wall of the cassette and to provide a fit sufficiently tight to prevent the needle 1 from disengaging from the cassette wall.
Figure 3B:
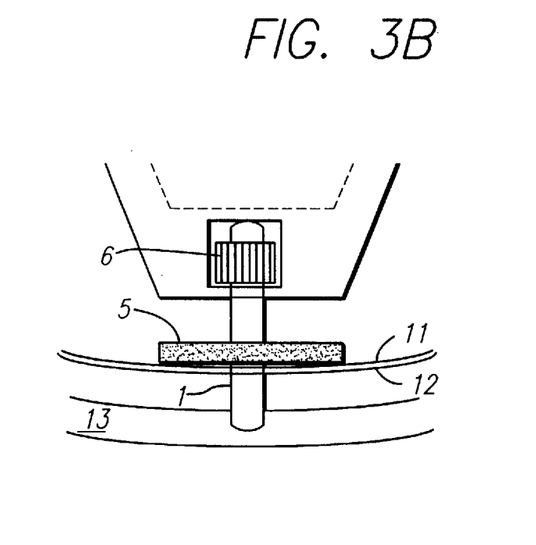
FIG. 3B depicts a cassette comprising a needle 1 engaging a subject to obtain a biological sample. The cassette is optionally encased or surrounded by an applicator having a wall 16 or external surface. The needle 1 is optionally surrounded by a stopper 5 to prevent penetration beyond the blood vessel 13 of the subject.
Figure 3C:
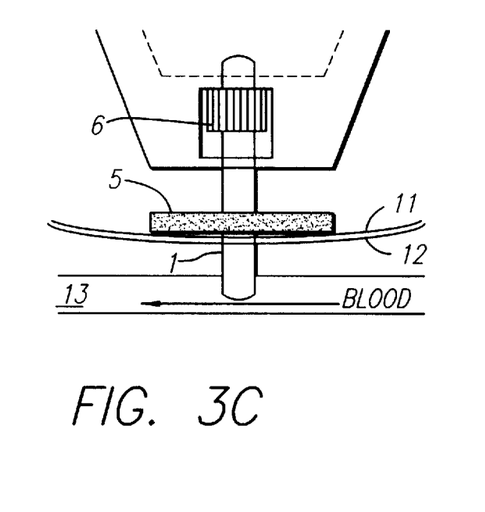
FIG. 3C depicts the cassette in operable position with respect to the subject for obtaining a suitable blood sample from the same.
Figure 3D:
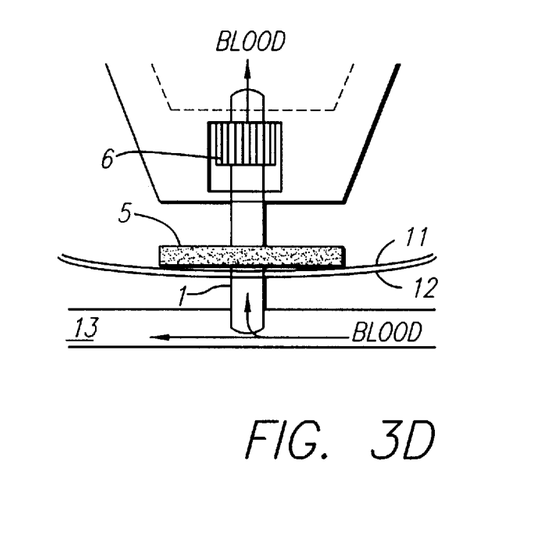
FIG. 3D depicts blood from a subject passing through the needle 1 into the cavity 4 of the cassette.

The cassette according to the present invention is preferably evacuated as is demonstrated by FIG. 2. The volume of the cassette cavity 4 may be adjusted to accommodate the assay or series of assays to be performed. A vacuum may be created during assembly of the cassette, or it may be created by means provided after assembly but before a biological sample is obtained. After the needle 1 is inserted into a subject's blood vessel 13, a stopper 5 is pressed against the subject's skin 12 as shown in FIG. 3 or against an applicator 11 as shown in FIG. 3. At such time, a septum or membrane 7 inside the sample cassette is punctured so that a biological sample, often blood, can enter into the sample cassette. A vacuum cassette facilitates the movement of the biological sample from the subject into the cassette cavity 4.

In preferred embodiments, an applicator is used in conjunction with the cassette as represented in FIG. 4. An applicator expedites handling the cassette which otherwise might be difficult because of the small size of the cassette. Using an applicator in conjunction with the cassette also helps to avoid contamination of the biological sample and helps ameliorate unnecessary pain to the subject.

Preferably, a means is provided to prevent or reduce backsliding of the sample cassette within the applicator used in conjunction therewith. One way of preventing or reducing backsliding of the sample cassette within the applicator is to provide corrugations 10 such as those represented in FIG. 2.

A plug 8 or a piston 38 may be provided in the cassette. When the cassette is in an analyzer, the plug 8 may be removed thereby facilitating transfer of the biological sample into the analyzer. Alternatively, instead of having a premade vacuum, when the cassette is compressed by an applicator, the needle 1 may be inserted into the patient and the compression released to create the vacuum in situ. Also, a vacuum may be created by a piston 38 (FIG. 9) that may be partially or totally removed while the needle 1 is engaging the subject to obtain a biological sample. Thereby, a vacuum may be premade or created by moving one or more walls of the cassette away from the subject while the needle 1 engages the subject for obtaining a biological sample.

The applicator used in conjunction with the sample cassette is preferably pen shaped as illustrated by FIG. 4. In other embodiments, the applicator may be flat. In preferred embodiments, all or most of the sample casette is housed inside the applicator. The needle 1 may be covered by a tubing that may be removed before obtaining biological samples. Tubing can be used for obtaining some biological samples such as urine from subjects or from containers.

In some preferred embodiments, the applicator has a means for puncturing the membrane or septum of the sample cassette after the needle 1 is inserted into the subject to obtain the biological sample. This means for puncturing in some instances may be a springloaded button that is used to puncture the septum or membrane in the sample cassette after the needle 1 is inserted into a blood vessel 13. Additionally, the applicator may provide one or more supports 14 to stabilize the cassette while obtaining a biological sample. For instance, when the needle 1 is inserted into a blood vessel 13, the cassette is between the front part of the applicator and one or more supports 14.

Figure 4A:
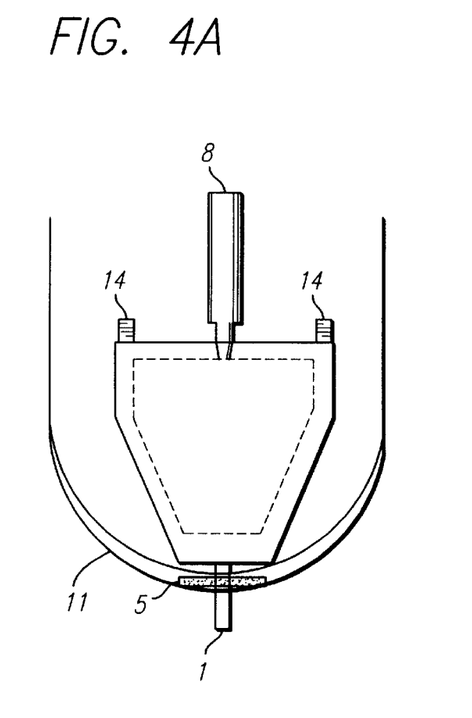
FIG. 4A is a front view and FIG. 4B is a side view depicting the cassette substantially housed in an applicator device whereby the means for obtaining a biological sample may protrude through an aperture in the applicator. An optional stopper 5 may impinge upon an inner surface of the applicator. One or more supports 14 may be provided to maintain the cassette in a desired position with respect to the applicator. Additionally, a plug 8 may be provided in connection with the cassette.
Figure 4B:
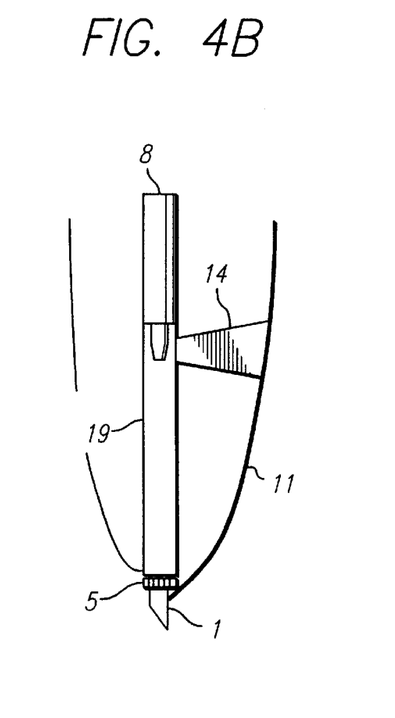
Figure 4C:
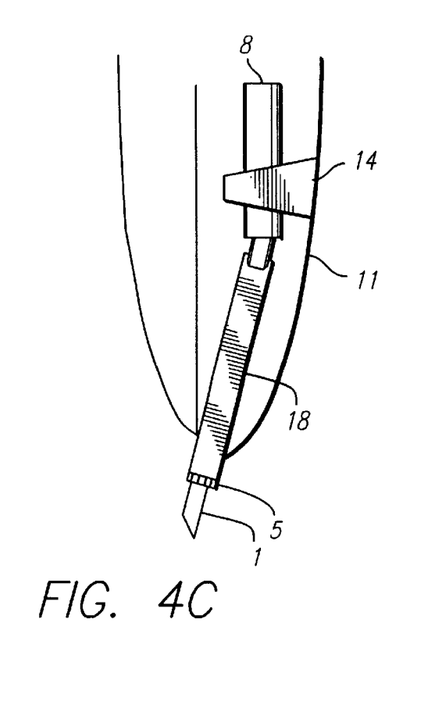
FIG. 4C depicts that an aperture may be provided in the applicator to allow for easy removal of the cassette.
Figure 4D:
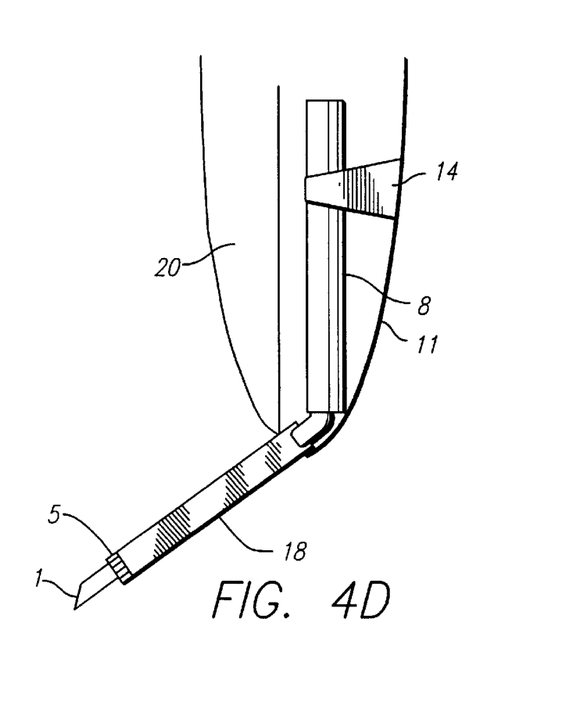
FIG. 4D depicts passage of the cassette from the interior of the applicator to the exterior of the applicator through an aperture properly placed and of the appropriate size to allow passage of the cassette through the same.

Alternatively, compression of the cassette may be released thereby creating a vacuum. When the cassette has been filled with a biological sample, the sample cassette may be all or partially ejected from the applicator by using the same or another button. Preferably, the sample cassette is tilted with respect to the long axis of the applicator after being all or partially ejected from the applicator as is shown in FIG. 4D. Arranging an applicator to eject the sample cassette at less than a 180 degree angle facilitates pushing the cassette into an analyzer disk.

In some instances, the biological sample must be transferred from a cassette into an analyzer disk when the disk is rotating in a CD or DVD player. Air or liquid must in turn replace the biological sample in the sample cassette. In order to accomplish this, it is preferable to provide a second hole in the sample cassette 23. There can be a plug 8 that is pulled off as a last step when inserting the sample cassette into an analyzer disk as is shown in FIG. 4. Alternatively, a hole can be punctured when the cassette is applied into the analyzer disk. For instance, instead of a plug, some embodiments of the invention feature a needle that punctures a septum. When the applicator is removed from the sample cassette, the needle places one or more small holes in the cassette. Either means allows the flow of the biological sample from the cassette into the analyzer.

Figure 5A:
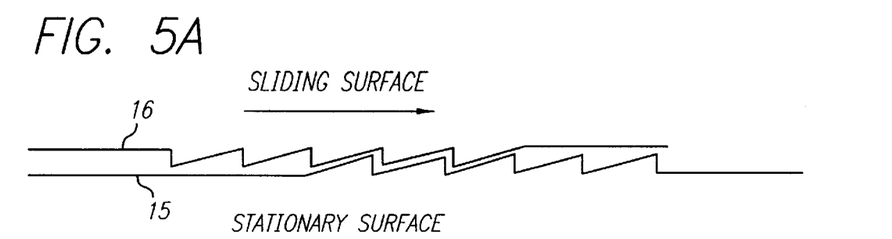
FIG. 5A demonstrates movement of a sliding surface 16 over a stationary surface 15 in a direction that is desirable.
Figure 5B:
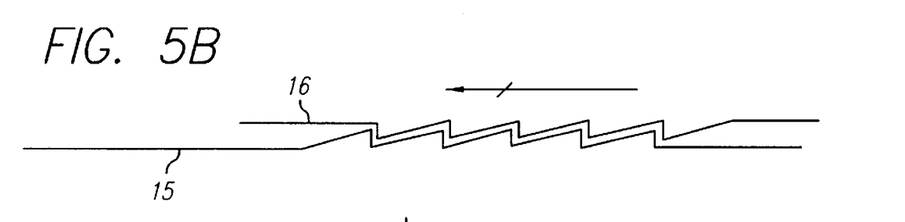
FIG. 5B demonstrates movement of a sliding surface 16 over a stationary surface 15 is prevented in a direction that is undesirable.

In preferred embodiments of the cassette and applicator, a means is provided to insure that the cassette is not reused once it has been contaminated with a biological sample. In order to prevent reuse of the contaminated cassette, it may be locked into the analyzer disk so that it cannot be easily removed. A means for locking the sample cassette in the analyzer disk preferably features a mechanical rectifier. Such a mechanical rectifier is demonatrated in FIG. 5 as surfaces 15 and 16 that are corrugated. Surfaces corrugated in such a manner glide easily in one direction but not at all in the other direction.

The sample cassette may feature markings such as stripes on one or more surfaces that substantially match similar markings on the surface of the analyzer disk. Hence, once a cassette is situated properly in relation to the analyzer disk, those markings form a unified pattern. Also, some embodiments of the cassette feature a means for engaging the cassette in the analyzer disk. Preferably, such a means for engaging provides a noise signal when the sample cassette is securely engaged with the analyzer disk. Hence, both visual and noise signals may be provided to insure that the sample cassette is in its proper position relative to the analyzer disk.

The cassette may contain such additional items as preloaded reagents, a battery or other electrical or microelectromechanical components that may be used for assaying the biological sample. Exemplary microelectromechanical components include, but are not limited to light sources, such as lasers and light emitting diodes, assay elements, microprocessors, electrodes, pumps, and valves. Preloaded reagents may be localized in separate compartments as solids or dissolved into water or a buffer. Likewise, the preloaded reagents may be stored inside a gel from which they are extracted by the sample. The analyzer disk may itself contain reagents, however, when the same analyzer disk is used repeatedly, it is preferable to put some or all of the reagents inside the sample cassette. Such is the case when the disk contains several assay sectors, which can be used one by one.

Reagents may also be added, for example, through an air inlet port or through a separate septum 20 which may be a feature of some embodiments of the present invention. Reagents are preferably circulated through the sample cassette in order to extract substantially all of the biological sample out of the casette. A disinfectant may also be added into the cassette to kill pathogenic agents and prevent microbial growth before the disposal of the analyzer disk. Suitable disinfectants include sodium azide, octadecyl trimethyl ammonium bromide and Kathon (Room and Haas Company) though it is contemplated that any known disinfectant may be suitable.

The following definitions are provided to further clarify the invention, but are not intended to be limiting.

The term "biological sample" as used herein is intended to encompass all samples obtained from living organisms such as blood, urine, cerebrospinal fluid, saliva, lymph tissue, extracellular fluids, intercellular fluids, etc. The term "cassette" as used herein is meant to describe the embodiments of an apparatus for collecting biological samples that are particularly designed for engaging a disk such as a CD or DVD disk and thereby providing an operable means for analyzing a biological sample by a CD or DVD player.

The term "evacuated cassette" is meant to describe a cassette according to the present invention wherein the cavity has an atmospheric pressure that is lower than the atmospheric pressure of the surrounding environment.

DESCRIPTION OF PREFERRED EMBODIMENTS

The following provides more detailed description of some of the preferred cassettes and applicators according to the present invention.

Casette 1

One preferred sample cassette according to the present invention is depicted in FIGS. 7A–7C. The sample cassette has one needle 1 and two septums 20 and 21. The needle is permanently fixed. The septums may be of any suitable size or shape and may be composed of any appropriate material. In fact, the septums may be just thinner areas of the wall of the sample cassette and therefore be composed of the very same material as other areas of the wall. Preferably, the sample cassette may be compressed while it is inserted into a blood vessel as FIG. 8 depicts. Thus, the sample cassette is preferably made of an elastic plastic material such as polyethylene, polypropylene or polyvinylchloride. Also preferably, the sample cassette is substantially transparent or semitransparent so that filling with a biological sample can be visually confirmed.

Figure 7:
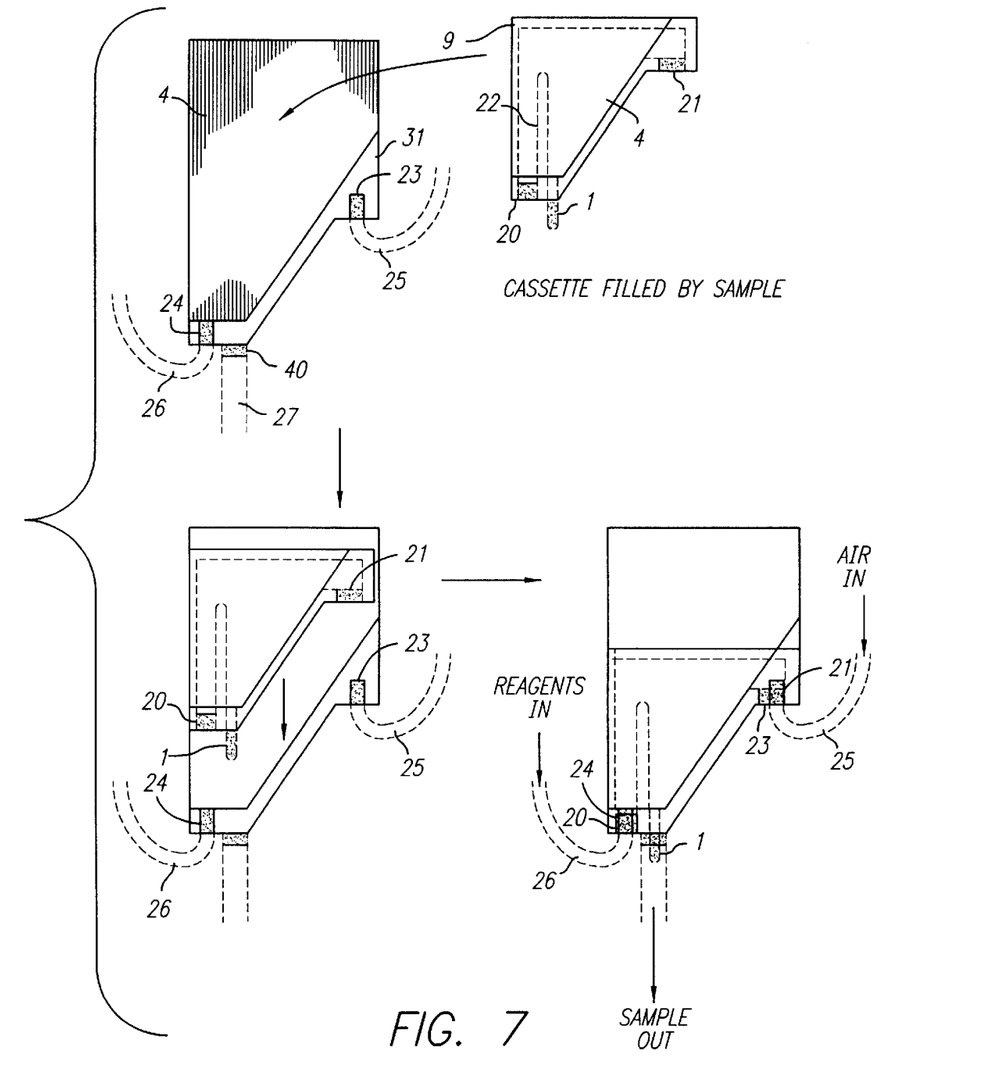
FIG. 7 depicts a sample cassette arranged in connection with tubes to allow entry and exit of a biological sample.
Figure 8A:
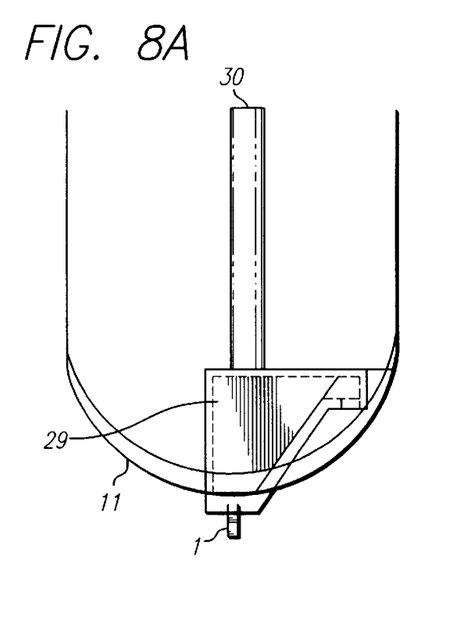
FIG. 8A depicts a front view and FIG. 8B depicts a side view wherein the cassette 29 is positioned in relation to the applicator surface 11 to allow the needle 1 to protrude to the exterior of the applicator for obtaining a biological sample.
Figure 8B:
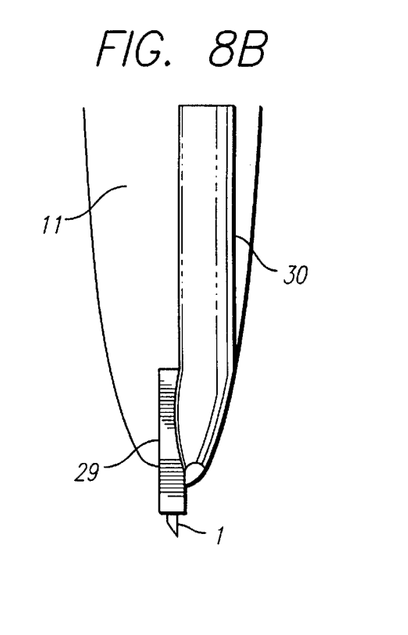
Figure 8C:
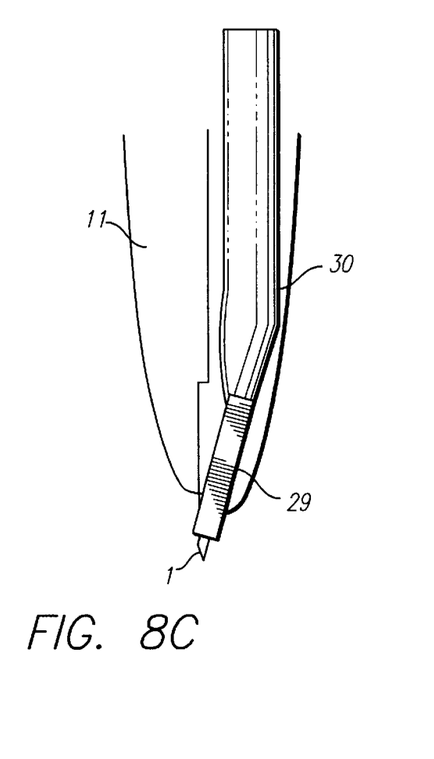
As shown in FIGS. 8C and 8D, rods 30 may serve as a means for creating a vacuum within the cassette and may serve as a means for pushing the cassette out of the applicator through an aperture positioned to accommodate passage of the cassette.
Figure 8D:
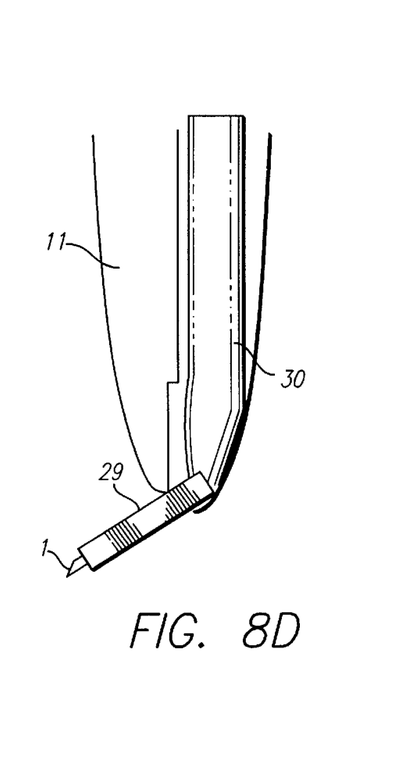

The cassette preferably has a wall or partition 22 inside. The wall or partition may function to circulate incoming reagent solutions through a first tube 26, a needle 24 and a septum 20 so that the biological sample is flushed out of the sample cassette through a second tube 27. Replacement air may enter into the sample cassette through a third tube 25, a needle and a septum 21. In each case the septum may be punctured by a separate needle.

An edge of the cassette may be inclined so that it will fit under the lid 31 of the cassette cavity in an analyzer disk. This lid 31 serves to guide the cassette while it is pushed into its final position and to lock the cassette into the plane of the disk together with the three needles 1, 23 and 24. Hence, this insures the easy transfer of reagents into the cassette, removal of biological sample and replacement with air.

Backsliding of the sample cassette may be prevented by a properly placed shoulder in the analyzer disk or corrugated sides 10 on the cassette so that gliding is allowed in one direction but not in the opposite direction. Mechanical rectification, i.e. corrugated sides is demonstrated in FIG. 5. One or all of the needles in the analyzer disk can be harpoon shaped. These three characteristics together prevent any accidental or purposeful removal of the cassette from the analyzer disk.

One or more of the needles associated with the analyzer disk need not be metal. Rather they may be molded as an integral part of the analyzer disk. Typically the disk is made of polycarbonate or a similar material.

Applicator

The cassette of the present invention may be used alone, but an applicator is used in conjunction therewith in preferred embodiments. One embodiment of the applicator is depicted in FIGS. 8A–8D. Preferably, a part of the applicator is transparent so that the sample cassette 29 can be seen visibly from outside the applicator. The transparent part may be lens shaped in some embodiments so that the cassette is magnified. This allows better observation of the filling of the sample cassette with the biological sample. The cross-section of the applicator is rectangular or oval in preferred embodiments. Also, preferably the applicator is about the size of a pen and is shaped so that it is comfortable in hand.

In preferred embodiments the applicator has a button on the end opposite the sample cassette. The button is preferably spring loaded. Thus, when the button is lightly pushed, one or more operably linked compression rods 30 will pull up, and a partial vacuum will be created in the cassette. After the sample is in and the cassette is ready for insertion into the analyzer disk, the button may be pressed, and the compression rods 30 serve then as pushing rods. The rods may be shaped so as to guide the cassette in a preset exit route. Preferably, one or more exit slits are shaped so that the sample cassette will be tilted when it is pushed out of the applicator as demonstrated in FIG. 8D. This facilitates the proper positioning of the cassette into the analyzer disk. The applicator may then be used as a tool to push the cassette into its final position in the analyzer disk. Thus, preferably the applicator is designed so that there is no need to touch the cassette by hand at any time while the sample is taken or analyzed.

Cassette 2

A vacuum sample cassette is especially preferred for use in accordance with the present invention. A vacuum sample cassette has at least three components: a bottom 2, a lid 3, and a needle 1. The needle 1 may be substantially blunt ended thereby resembling a capillary. These components are normally all three premade separately. The cassette can be molded in one step. However, to guarantee a constant volume two or more steps are preferred. Two pieces of plastic 5 and 6 are molded around the needle. One is a stopper 5 that prevents the needle from penetrating too deep into a skin and while stopping the penetration will force the puncturing of the inner wall of the sample cassette. The other piece 6 prevents the needle from sliding out of the sample cassette, facilitates the gliding and guides the needle inside the sample cassette.

The cavity 4 provides a desired volume for containing a biological sample. There may be separate wells for one or more reagents in some embodiments. The wells may have walls of appropriate height so that they are substantially closed by the cover when a vacuum exists inside the sample cassette but open when the cassette is filled with a biological sample. The cassette may also have passive supporting structures so that it does not collapse when a vacuum is produced inside the cassette cavity. Sidewalls of the sample cassette may have a groove 18 that substantially surrounds the container.

The cover is usually flat except for a ridge 17 in the perimeter that substantially fits the groove. The inner surfaces of the container and lid may be coated with any variety of compounds suited to the particular application to which the sample cassette is to be used. For instance, the surfaces can be laminated with such substances as ammonia plasma and/or they may be treated by an excess of 1,4-phenylene di-isocyanate. The excess reagent may be washed away and heparin may be added. Thus, the surface may be covered by immobilized heparin that is useful to inhibit blood coagulation.

Figure 6:
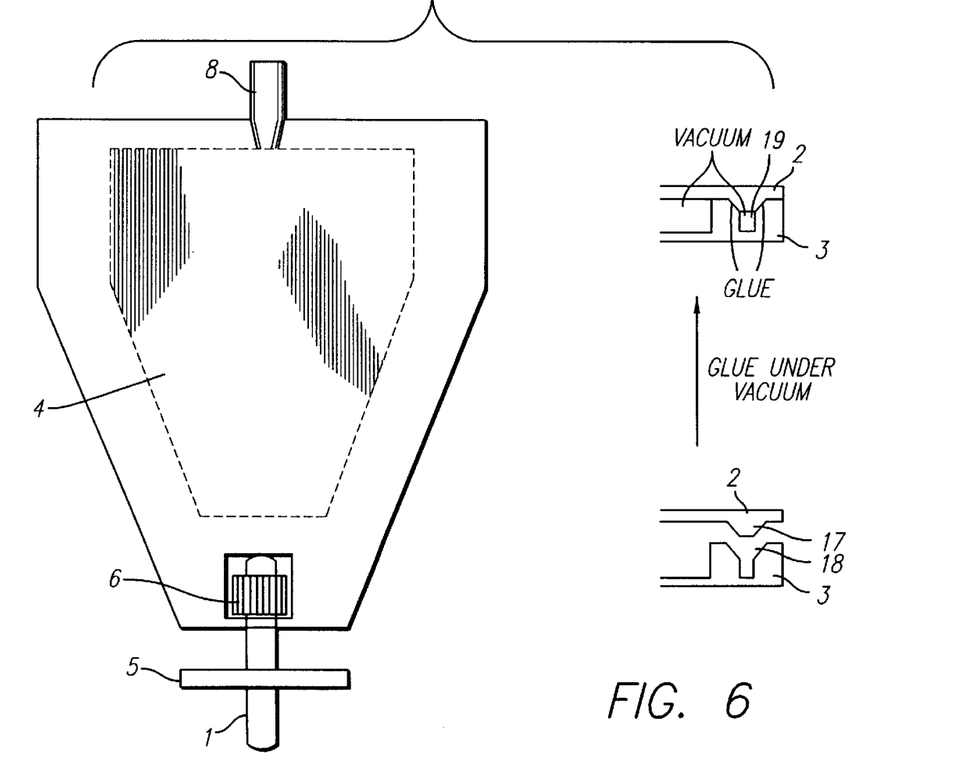
FIG. 6 represents a vacuum sample cassette according to some preferred embodiments of the present invention. There a lid 2 having a ridge 17 is provided for engaging a groove 18 of the cassette wall. Such an arrangement allows creating and maintaining a vacuum in the cassette cavity 4.

In order to assemble a sample cassette according to the present invention, desired reagents are loaded into the container followed by the needle(s) 1 and optional other components. The ridge 17 on the cover may be treated with glue and the container 3 and lid 2 pressed together under vacuum. The glue may be cured either thermally or by UV-light. Optionally a plug 8 of the applicator is positioned in its place in the sample cassette before the container and cover are glued together. The sample cassette depicted in FIG. 6 is symmetrical. It may be permanently evacuated during manufacturing, for instance, by closing the cassette by a plug in a vacuum chamber. The double ended needle 1 may have a collar that may be used to push the needle through the thin wall of the sample cassette after the other end of the needle is inserted into the subject or some sample. The push button of the applicator is normally pushed downward during the sample collection.

After the sample cassette is filled with a biological sample, it is normally pushed out of the applicator. To initiate the final exit of the cassette, a sufficiently strong force must be applied on the button. Alternatively, the button may be shaped so that there is a small shoulder on one side of the button and a small sideward movement is needed to push the cassette out of the applicator. Hence, the applicator may be so designed and the sample cassette so positioned as to exit substantially horizontally as depicted in FIG. 4. When the sample cassette is in its final position, the applicator is pulled back and at the same time the cassette is unplugged. In some embodiments, the evacuated cassette may have a septum for air intake instead of a plug.

Cassette 3

Figure 9A:
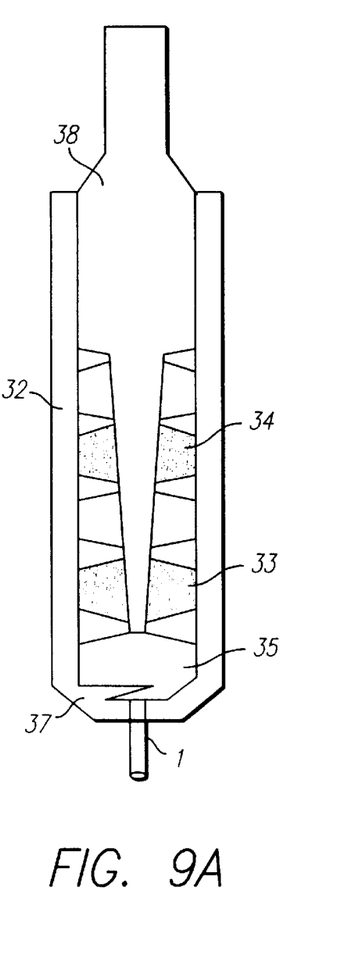
FIG. 9A demonstrates that two or more reagents may be preloaded.
Figure 9B:
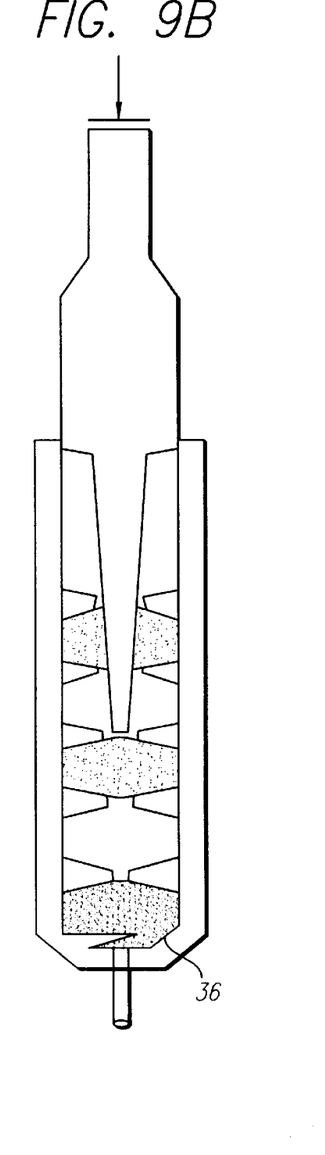
FIG. 9B demonstrates that by pulling piston 38 while the needle 1 is in a capillary, the sample compartment 35 may be filled.
Figure 9C:
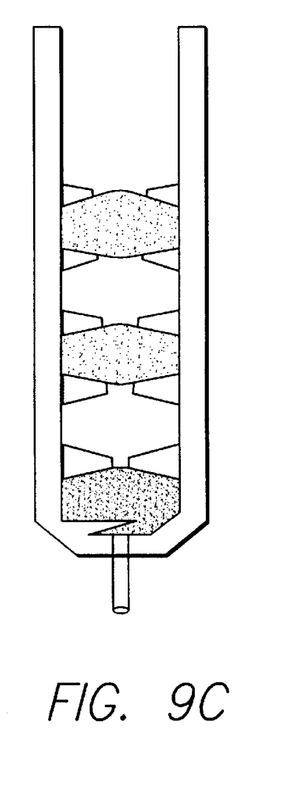
FIG. 9C demonstrates that the piston 38 may then be completely removed.

A sample cassette substantially in the shape of a syringe may be used in accordance with the present invention. A vacuum may be created by pulling a piston 38 while a needle 1 substantially engages a subject for obtaining a biological sample 36. In some embodiments, a tube may be connected to or operably linked with the needle 1. Such a cassette may be prepared by a laminating process and may be formed of three layers. The middle layer 32 is depicted in FIG. 9. The top and bottom layers may have substantially the same external shape as the middle layer 32. However, the top and bottom layers may be larger or smaller than the middle layer 32 to facilitate inserting a cassette disk into an analyzer. The top and bottom layers normally create a substantially closed structure upon assembly with the middle layer 32.

A cassette in accordance with this embodiment may be adapted for engagement with an applicator. Alternatively, a piston 38 may be formed in such a shape and size as to function as an applicator. The piston 38 may be corrugated so as to prevent it from sliding back when the cassette is assembled into an analyzer disk.

Appropriate reagents and washing agents for conducting the desired assays may be provided as desired. As shown in FIG. 9, for example, a reagent 33 and a washing solution 34 may be provided in such a spatial orientation as to move upward one or more cavities as the biological sample 36 enters the cassette. A barrier 37 may be provided to prevent premature mixing of the biological sample 36 and the reagent 33 or washing solution 34. Such a barrier may be of any desired material or thickness as one of skill in the art readily appreciates. Preferably, the cassette is designed so that the sample 36 and desired reagents 33 and washing solutions 34 enter the analyzer sequentially in the desired order.

The embodiments described herein are purely exemplary. One skilled in the art may make many variations and modifications to the embodiments described herein using functionally equivalent components to those described. Though intended for use with CD or DVD players for biological sample analysis, one could make similar cassettes and applicators for use with functionally equivalent players as such are developed. Moreover, though primarily designed for biological sample collection and analysis, the cassette and applicator might easily be applied to analysis of other substances if desired. The invention having been described with particular reference to the preferred embodiments, the scope of the invention is limited only by the following claims.

What is claimed is:

1. An apparatus for collecting a biological sample from a subject for subsequent transfer to a CD or DVD, said apparatus comprising:
   (a) a cassette comprising walls which define a cavity for receiving said biological sample, said cassette being adapted to engage said CD or DVD;
   (b) an inlet for transferring said biological sample from the subject into said cavity; and
   (c) an outlet for transferring said biological sample from said cavity to said CD or DVD when said cassette is engaged with said CD or DVD.

2. An apparatus according to claim 1 wherein said cassette comprises a mechanical rectifier which locks said cassette in engagement with said CD or DVD.

3. An apparatus according to claim 1 wherein said inlet comprises a conduit having a first end for penetrating said subject and a second end for penetrating the wall of said cassette which defines said cavity.

4. An apparatus according to claim 1 which further comprises a reagent or washing solution for said sample.

5. An apparatus according to claim 1 which further comprises an electrical component or microelectromechanical component.

6. An apparatus according to claim 1 which further comprises an applicator for housing said cassette prior to engagement of said cassette with said CD or DVD.

7. A CD or DVD comprising:
   (A) a disk body having a surface adapted to engage an apparatus which contains a biological sample for transfer to said CD or DVD; and
   (B) an apparatus engaged with said surface of said disk body, said apparatus comprising:
      (a) a cassette comprising walls which define a cavity for containing said biological sample;
      (b) an inlet for introducing said biological sample into said cavity prior to engagement of said apparatus with said surface of said disk body; and
      (c) an outlet for transferring said biological sample from said cavity to said CD or DVD when said apparatus is engaged with said surface of said disk body.

8. A CD or DVD according to claim 7 wherein said cassette comprises a mechanical rectifier which locks said cassette in engagement with said surface of said disk body.

9. A CD or DVD according to claim 7 wherein said inlet comprises a conduit having a first end for receiving said biological sample and a second end for penetrating the wall of said cassette which defines said cavity.

10. A CD or DVD according to claim 7 wherein said apparatus further comprises a reagent or washing solution for said sample.

11. A CD or DVD according to claim 7 wherein said apparatus further comprises an electrical component or microelectromechanical component.

12. A method for transferring a biological sample from a subject to a CD or DVD, said method comprising the steps of:

transferring the biological sample from the subject to a cavity of a cassette;

engaging said cassette with a CD or DVD; and transferring the biological sample from said cassette to said CD or DVD.

13. A method according to claim 12 wherein said cassette further comprises a reagent or washing solution, said method comprising the step of contacting said reagent or washing solution with said biological sample located with said cavity of said cassette.

14. A method according to claim 12 which comprises the step of locking said cassette in engagement with said CD or DVD.

15. A method according to claim 12 wherein said cassette further comprises a conduit having a first end and a second end, wherein said method comprises the steps of penetrating said subject with said first end and penetrating a wall of said cavity of said cassette with said second end to provide transfer of said biological sample from said subject to said cavity.

16. A method according to claim 12 wherein said cassette further comprises an electrical component or microelectromechanical component, said method comprising the step of treating said biological sample located in said cavity of said cassette with said electrical component or said microelectrochemical component.

* * * * *